(12) United States Patent
Berger et al.

(10) Patent No.: US 9,364,304 B2
(45) Date of Patent: Jun. 14, 2016

(54) CLEANING DEVICE

(71) Applicant: FERTON HOLDING S.A., Delemont (CH)

(72) Inventors: Edouard Berger, Vernier (CH); Quaderdan Wakil, Nyon (CH); Pierre Fridez, Froideville (CH); Marcel Donnet, Saint Jean de Gonville (FR); Abul Kalam Mohamed Zahir, St-Cergue (FR)

(73) Assignee: FERTON HOLDING S.A., Delemont (CH)

( * ) Notice: Subject to any disclaimer, the term of this patent is extended or adjusted under 35 U.S.C. 154(b) by 9 days.

(21) Appl. No.: 14/332,961

(22) Filed: Jul. 16, 2014

(65) Prior Publication Data
US 2015/0034135 A1   Feb. 5, 2015

(30) Foreign Application Priority Data

Aug. 1, 2013   (DE) .......................... 10 2013 108 295

(51) Int. Cl.
*A61C 19/00*   (2006.01)
*B05B 15/02*   (2006.01)

(52) U.S. Cl.
CPC ............. *A61C 19/002* (2013.01); *B05B 15/025* (2013.01); *B05B 15/0275* (2013.01)

(58) Field of Classification Search
CPC ...................................................... A61B 19/34
See application file for complete search history.

(56) References Cited

U.S. PATENT DOCUMENTS

| 5,472,666 A * | 12/1995 | Slaby .................. A61C 19/002 134/170 |
| 2004/0118440 A1* | 6/2004 | Sasaki .................... A61B 19/34 134/166 C |

* cited by examiner

*Primary Examiner* — Jason Ko
(74) *Attorney, Agent, or Firm* — Arent Fox LLP

(57) ABSTRACT

A cleaning device, especially for cleaning clogged nozzles of dental devices, with a base body, which comprises a main channel, wherein the main channel is designed for the transport of a medium, especially a fluid, characterized in that the base body, at a first end, has a receiving zone, wherein the receiving zone is designed for the arrangement of another member, especially a clogged dental device, and in that the main channel has an access zone, through which the medium may be fed into main channel and/or the pressure thereof may be raised.

13 Claims, 4 Drawing Sheets

CLEANING DEVICE

CROSS REFERENCE TO RELATED APPLICATION

Figure 1:
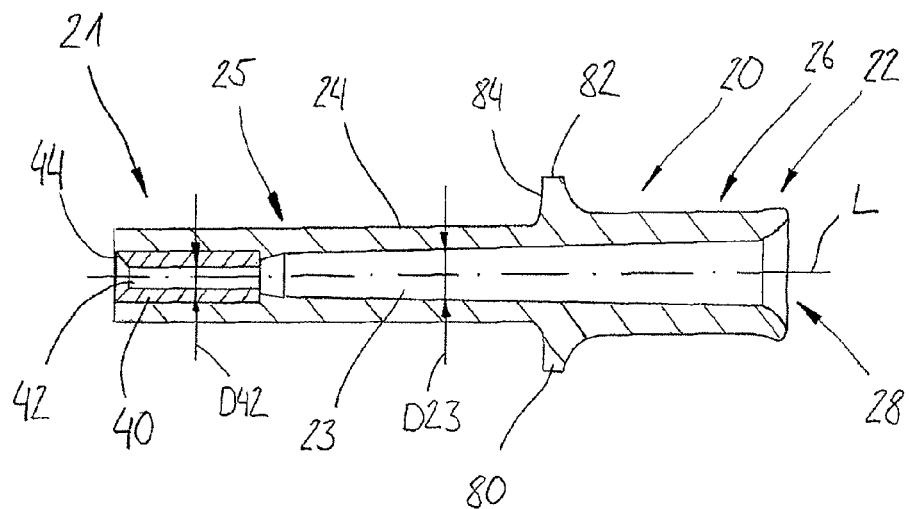

This application claims priority to German Patent Application No. 10 2013 108 295.5, filed Aug. 1, 2013, the disclosure of which is hereby incorporated by reference in its entirety.

The present invention relates to a cleaning device, especially for cleaning clogged nozzles of dental devices, a medical apparatus having a cleaning device, as well as the use of a cleaning device.

Cleaning devices of the above-mentioned type have been known in various configurations from prior art. For example, they have been used in powder jet devices, such as employed in the field of dental medicine. If powder jet devices will not be maintained, the hand piece or the nozzle tube thereof may become polluted or clogged by lumps of powder with time. Therefore, proper operation will not be ensured. Known cleaning devices are operated with specific cleaning powders, which are sprayed through the hand piece or the nozzle tube, respectively. However, cleaning capacity of such systems is very limited as dissolving capacity of the cleaning substance often is not sufficient to eliminate persistent clogging. Furthermore, this requires the cleaning procedure to be redone very frequently. It is true that mechanical systems, which for example function with specific cleaning needles, are suitable for dissolving heavy pollutions; however, there is the risk of damaging the interior of the hand piece or the nozzle tube, respectively, by the hard cleaning needle. It is of course possible to clean the hand piece or nozzle tube, respectively, in an ultra sound bath, but this gives rise to great effort of (dis)assembling and expenditures of time and cost.

It is thus an object of the present invention to provide a cleaning device, especially for cleaning clogged nozzles of dental devices, a medical apparatus having a cleaning device, as well as the use of a cleaning device overcoming the above-mentioned disadvantages, and which may be employed for a wide variety of different medical devices, especially for a wide variety of different powder jet devices.

This object will be achieved by a cleaning device, especially for cleaning clogged nozzles of dental devices, according to claim 1, a medical apparatus according to claim 12, as well as a use of a cleaning device according to claim 13. Further advantages and characteristics of the invention will become apparent from the dependent claims as well as the description and the accompanying figures.

According to the invention a cleaning device, especially for cleaning clogged nozzles of dental devices, having a base body comprising a main channel, the main channel being designed for transportation of a medium, especially a fluid, is characterized in that the base body, at a first end, has a receiving zone, the receiving zone being designed for the arrangement of another member, especially a clogged dental device, and in that the main channel has an access zone, through which the medium may be fed into the main channel, and/or the pressure of which may be raised. Thus, the basic principle is based on that a medium or a fluid, respectively, wherein the fluid is advantageously water, is passed or sprayed with (high) pressure through a hand held device (especially of a dental device) which is to be cleaned, and/or a clogged nozzle tube, so as to dissolve and remove impurities.

Alternatively, it is preferred that the medium is a (cleaning) powder or water, which is blended therewith. Advantageously the base body of the cleaning device extends along a longitudinal axis and has a length of about 50 to 80 mm, preferably about 55 to 70 mm, most preferably about 60 to 65 mm. The arrangement of the cleaning device is suitably done via the base body's first end, which may be arranged within the other member. Advantageously the receiving zone may accommodate or encompass, respectively, parts of the device to be cleaned. Advantageously the nozzle tube, which is to be cleaned, may for example be arranged in the receiving zone. The cleaning procedure in itself is done through the pressure of the medium in the main channel or by passing the medium along the main channel towards the nozzle tube to be cleaned.

For this end, the main channel advantageously has the access zone, through which the medium may be fed and/or the pressure of which may be raised. Especially preferably, the main channel in itself forms the access zone. By this it is meant, that the access zone is formed in elongation of the main channel as an opening at a second end of the base body, wherein the second end is located along the longitudinal axis opposite of the first end. Accordingly, the main channel entirely passes through the base body along the longitudinal axis. However, in an alternative way, the main channel may preferably not pass entirely through the base body. Accordingly, the base body is closed at the second end and the access zone is arranged between the first and second end. In this case, the access zone is essentially formed as a radial access in the main channel while the base body is closed at the second end. This radial access may for example be a bore or the like, which is suitable for filling the main channel with the medium.

The access may also be provided with a thread or the like, to be able to be screwed into an appropriate cover. Pressure built-up or transport of the medium toward the first end, respectively, is advantageously done by an actuating device, which may be a component of the cleaning device; or by a pressure device, which may be arranged at the cleaning device. The different possibilities will be described in detail below. Basically, the pressures for cleaning are in a range of about 4 to 15 bar, preferably 7 to 12 bar, eventually even higher than 15 bar.

It is to be understood that the cleaning device, more specifically the base body must be fabricated from an appropriate material, to withstand the pressures. Preferably, the base body is fabricated from a plastic material having the appropriate properties. It is especially advantageous if the cleaning device is fabricated from material(s), which in addition may be sterilized. Advantageously, the materials employed are in addition temperature resistant. Advantageously, the required mechanical strength also becomes achievable by forming or shaping the base body, respectively. Thus, the base body, at its outer periphery, may have bars, grooves, recesses and the like, to control the mechanical strength.

Advantageously, the cleaning device is characterized in that the receiving zone has a receiving channel and in that a diameter of the main channel is greater than a diameter of the receiving channel. Thus, arrangement of the above-mentioned nozzle tube is advantageously done in the receiving channel. Advantageously the diameter of the main channel decreases towards the receiving zone. Preferably, the main channel has a diameter of about 4 to 5 mm, especially preferably about 3.5 to 4 mm, in a range in which the access zone is formed. In an especially preferred embodiment the access zone (or the main channel, respectively) is increased to a diameter of 6 to 7 mm and more, towards the second end of the base body. This allows and improves arrangement of pressure means. Advantageously, the diameter of the main channel, towards the arrangement zone, is about 1.5 to 3 mm, especially preferably about 2 mm. Advantageously, at the first end, the receiving channel directly connects to the main channel, that is, it virtually extends it. A diameter of the receiving channel advantageously is in a range of about 1.5 to 2.5 mm, especially preferably at about 2 mm. It is to be understood that this value depends on the dimensions of the nozzle tube to be cleaned, and appropriately is adaptable to this. By decreasing the diameter of the main channel towards the receiving zone, the flow rate of the fluid may advantageously be increased during transport/pressure built-up. The high flow rate of the fluid and the high momentum resulting therefrom contribute, besides pressure of the fluid, to dissolve even heavy impurities. Advantageously, the receiving channel along the longitudinal axis has a length of about 5 to 20 mm, preferably about 7 to 15 mm, most preferably about 9 to 11 mm.

Suitably, the cleaning device is characterized in that in and/or at the access zone a pressure device, by which the medium may be passed into the main channel and/or the pressure of the medium may be raised, may be arranged pressure-tightly. Advantageously, the pressure device is a disposable syringe known from prior art having appropriate size. Advantageously, it may form-fittingly and pressure-tightly be arranged in and/or at the access zone, such that upon operating the pressure device, which suitably is filled with a specified amount of water, no medium will leak from between the base body and the pressure means. Advantageously, the cleaning device is initially be arranged at the apparatus to be cleaned. Following this arrangement, the (filled) pressure device is appropriately positioned and operated at the access zone. Especially preferably, the positioning or arrangement of the pressure device at the access zone, respectively, is performed by the user exerting a specified (manual) force. It is to be understood, that the access zone alternatively may also be provided with a thread or the like, allowing an appropriately configured pressure device to be screwed on tightly (basically, tightness refers to the above-mentioned pressures, which may reach values up to 15 bar and more).

Following arrangement of the pressure device, the actual cleaning procedure may be started. Suitably, the internal diameter of the access zone is made such that it slightly tapers towards the first end of the base body. In this way, form-fit and/or force-fit between the pressure device and the access zone may be improved and tightness may further be increased. It is to be mentioned, that the pressure device in this embodiment, on the one hand, is for filling the main channel with the medium. On the other hand, pressure built-up and transport of the medium may finally be achieved by means of the pressure device. Consequently, the medium is supplied through the access zone and the pressure thereof will be increased.

Also preferably, the cleaning device is characterized in that the base body has an actuation device, by means of which the medium may be transported and/or the pressure of the medium may be raised. The actuation device in itself is an integrated pressure device. A difference to the foregoing embodiment resides in that the medium generally will not be transported to the main channel through the actuation device. Thus, the pressure will not be increased via the access zone, but the access zone is for feeding the medium and is advantageously formed between the first and second end of the base body as an essentially radial opening in the base body, which opening creates an access to the main channel. The actuation device per se is suitably formed according to a known disposal syringe, but not as a separate component, but is integrally formed with the base body. Thus, advantageously the actuation device comprises a piston and a piston rod, which are arranged within the main channel, the piston rod advantageously being pressure tightly guided to the outside, such that operation from the outside, preferably by hand, is possible. By way of this operation, pressure built-up and transport of the medium, which is present in the main channel, towards the nozzle tube to be cleaned will be achieved. Thus, the main channel functions similar to a tank, wherein the tank suitably is filled via the access zone. Alternatively preferably, the actuation device or the piston rod, respectively, is not guided to the outside. In this way, also preferably, a pressurized air tubing or the like at the base body may be attached via a pressure connection, through which a pressure may be transferred by air or also by a liquid into the base body, whereby the internal actuation device is operable with great ease. The actuation device as such or the piston rod thereof, respectively, are not required to be guided to the outside of the base body.

For operating the pressure device as well as the actuation device a drive unit may suitably be incorporated into the cleaning device, for example one having a small electric motor or the like.

Suitably the cleaning device is characterized in that the base body, at an outer periphery, has a first and a second arrangement zone, wherein at least a cross section of the first arrangement zone is essentially round, and is especially circular. An outer diameter of the first arrangement zone is preferably in a range of about 4 to 12 mm. In particular, an outer diameter advantageously is in a range of about 4 to 8 mm, preferably at about 5 to 7 mm, most preferably at about 5.5 to 6 mm. Suitably, an outer diameter of the second arrangement zone is in a range of 6 to 12 mm, preferably at about 7 to 10 mm, most preferably at about 8 to 9 mm. The values mentioned above have great advantage in that the cleaning device in this way may be arranged in or at, respectively, a wide variety of dental devices. The first arrangement zone is advantageously the zone of the base body, which is arranged in the apparatus to be cleaned, whereas the second arrangement zone is the zone of the base body, that is hand-held by the user upon arranging the cleaning device at the apparatus to be cleaned or upon operating the cleaning device. It is thus of advantage for the second arrangement zone to be provided with an appropriate surface, for example having engravings or riffles, which may prevent the hand from slipping off. Preferably, an outer diameter of the second arrangement zone is round, circular, angular, or is formed convex or even concave along the longitudinal axis. Especially preferably, the outer diameter is also oval, at least in certain areas, allowing even better handling. In an especially preferred embodiment, the first arrangement zone is provided with four recesses, grooves or ribs, which are circumferentially partitioned, and extending along the longitudinal axis, causing stiffening of the base body in this region. The first arrangement zone may advantageously be provided with a thread or the like, to screw the cleaning device to the other element. This may significantly facilitate cleaning since the other element (e.g. the hand piece) and the cleaning device then will form an integral unit and are not required to be held together by the user. It is to be understood, that for this end, the respective other element, in this case the hand piece, must be provided with a corresponding counter-thread.

Preferably the cleaning device is characterized in that the base body comprises at least one centering unit which, at least in certain areas, extends essentially radially and/or parallel to the longitudinal direction of the base body, and which is especially designed for orienting and/or centering the base body relative to the other element, especially in a hand piece of a dental device. Preferably, the centering unit, at least in certain areas, is formed as a surrounding collar or ring, which has a diameter greater than the remaining base body. Preferably, the diameter of the centering unit is round or even circular, respectively, whereby centering advantageously may be done at appropriate functional surfaces within the other element. While centering it to align the centerline of the cleaning device with a centerline of the dental device to be cleaned or a nozzle tube to be cleaned, respectively, orientation refers to the arrangement of the dental device to be cleaned along the longitudinal axis as viewed relative to the cleaning device. In other words, the point is that the first arrangement zone protrudes into the dental device to be cleaned and that the distance or extension, respectively, of how far the first arrangement zone protrudes may be defined or determined, respectively, by the centering unit. Thus, the centering unit may also serve as a stop unit along the longitudinal axis. For this end, the centering unit is appropriately distant from the first end of the base body. The distance suitably is measured starting from the receiving channel in the direction of the centering unit parallel to the longitudinal axis. The centering unit may suitably be formed such that it provides a locking function, corresponding for example to a bayonet lock. Accordingly, the centering unit may provide a form- and/or force-fitting arrangement in relation to the other element.

Advantageously, the cleaning device is characterized in that the centering unit comprises at least one radial and/or at least one axial stopper surface. Preferably the centering is done via the at least one radial stopper surface, while orientation (along the longitudinal axis) is via the at least one axial stopper surface. The radial stopper surface advantageously extends essentially parallel to the longitudinal axis having a centering diameter, while the axial stopper surface advantageously extends transversally to the longitudinal axis. It is to be understood, that combination is possible as well, wherein the stopper surface may also be angular to the longitudinal axis, whereby the cleaning device may be oriented and centered relative to the other element. Preferably, at least one respective stopper surface is provided. By this, an arrangement of the cleaning device at a wide variety of dental devices may advantageously be performed, since the presence of 2, 3, 4, 5 or more radial and/or axial stopper surfaces allows orientation and/or centering at dental devices having a wide variety of internal diameters or a wide variety of lengths, respectively. It is to be understood, that the radial stopper surfaces should provide centering diameters as different as possible and that the axial stopper surfaces should provide axial distances as different as possible.

Preferably, the cleaning device is characterized in that the centering unit may be arranged and set along the longitudinal direction on the base body. Accordingly, the stopper surfaces may suitably be arranged along the longitudinal direction. By this, in particular the axial stopper surface(s) or the distance thereof at the beginning of the receiving channel, respectively, may be displaced. Advantageously, the centering unit thereof is provided as a separate component, which for example may be positioned on the base body via a thread. Alternatively, it may be displaced via appropriate guide rails and may be locked via suitable holding means.

Advantageously, the cleaning device is characterized in that the access zone may be separated from the main channel by the actuation device. For this, the piston of the actuation device along the longitudinal direction is positioned to the access zone such that upon pressure built-up or upon passing medium towards the nozzle tube to be cleaned, respectively, that part of the main channel, in which the medium is present, no longer is in contact with the access zone. Accordingly, the base body will automatically be tightly closed and the access zone is not required to be provided with a lid.

Suitably, the cleaning device is characterized in that the receiving zone and/or the access zone is formed of a material, which is softer than a material of the base body. Advantageously the base body is comprised of a core, which is fabricated of a plastic material having a hardness greater than 75, preferably greater than 80 Shore. Thereby, the core is sufficiently self-stable in order to accommodate high pressures. This core is advantageously surrounded by another plastic material, which advantageously has a hardness in a range below 75 Shore, preferably about 40 to 75 Shore. Advantageously, it is achieved by this "soft coat", that the apparatus to be cleaned will not be damaged upon arrangement through the cleaning device. Another advantage resides in that improved effect of leakproofness will be achieved by the softer coat, i.e. between the contact sites or the contact surfaces, respectively, of the cleaning device and the apparatus to be cleaned. The core of the base body may also consist of metal, which is coated or covered with a plastic material of the desired hardness.

Alternatively, the base body may preferably also completely consist of softer material. Harder plastic or metal parts are advantageously incorporated into that soft material for stiffening, thereby restoring the desired strength in the base body. Preferably, the receiving zone and/or the access zone has a hardness, which eventually is even lower than 40 to 75 Shore, especially lower than 40 Shore. This is equally true if the receiving zone and/or the access zone will be formed by the base body itself and if the receiving zone and/or the access zone will be formed as separate parts, which are located in the base body. This also allows improvement of leakproofness of the respective contact sites—or contact surfaces, respectively. All Shore values mentioned above are based on the measuring procedure A (i.e. Shore A or ShA).

Still preferably, the cleaning device is characterized in that the receiving zone and/or the access zone are form-fittingly and/or force-fittingly attached to the base body. Accordingly, the receiving zone and/or the access zone are suitably fabricated as separate components, which may be arranged or are arranged, respectively, in the base body. As to the access zone, this is especially true for the embodiment, wherein a pressure device is employed. In an especially preferred embodiment the receiving zone is fabricated as an essentially cylindrical component having an outer diameter of about 3 to 5 mm, especially preferably of about 3.5 to 4 mm. Preferably, for this end, a plastic material of about 75 to 40 Shore or even softer will be employed. It is to be understood that an outer diameter of the receiving section is not required to be round, but may have any shape, for example oval, angular, etc. as well. The same accordingly applies to an inner periphery of the base body, in which the receiving zone is advantageously arranged. In this embodiment the receiving zone, including its periphery, is fully integrated into the base body. The same also applies to the access zone, which may as well be formed as a separate component and may be integrated in the base body. As to the material or the materials, respectively, used for this, reference is made to what is set forth for the arrangement zone, wherein it is to be noted that the access zone advantageously is made slightly harder than the arrangement zone. It is to be understood that the receiving zone and/or the access zone may also be form-fittingly and/or force-fittingly arranged along the longitudinal direction offset to the base body, for example via a screw connection. The receiving zone and/or the access zone may at least be partially surrounded by the base body. Basically, for better arrangement of the nozzle to be cleaned, the receiving channel is provided with a rounding or bevel.

Advantageously, the cleaning device is characterized in that the base body comprises a pressure converter. Advantageously, the pressure converter is arranged within the main channel. Here, two pistons having differing piston areas are connected via the piston rod, whereby high pressure may be generated from low pressure. The principle has already been known from prior art. Suitably, said high pressure may be used for cleaning. The low pressure may be applied by the user's hand-held force. However, the base body may also comprise the pressure connection by means of which the (low) pressure present in the base body may be applied. Accordingly, the actuation device is not passed outwardly to the outside of the base body.

According to the invention, a medical apparatus comprises a cleaning device according to the invention. It is to be understood, that all advantages and characteristics of the cleaning device according to the invention also apply to the medical apparatus and vice versa. Especially preferably, the medical apparatus is a powder jet device for tooth cleaning.

According to the invention, the use of a cleaning device according to the invention is provided. It is to be understood, that all advantages and characteristics of the cleaning device according to the invention as well as of the medical device also apply to the use according to the invention.

Figure 2:
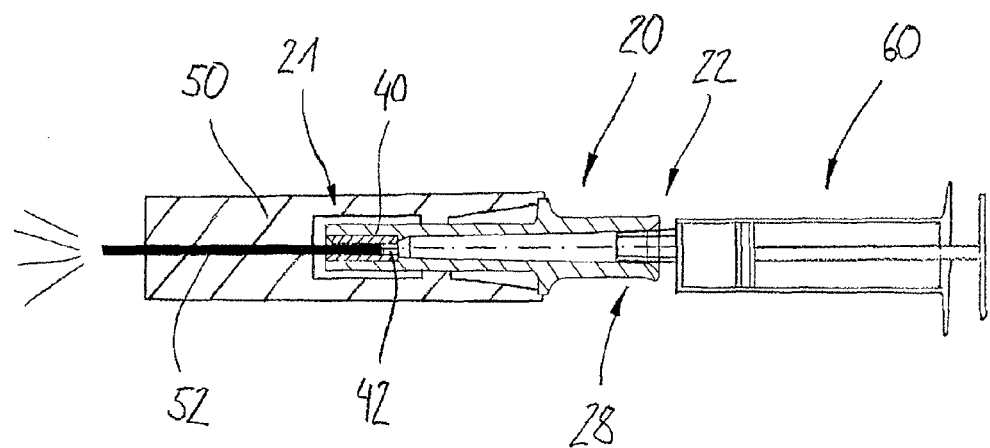
Figure 3:
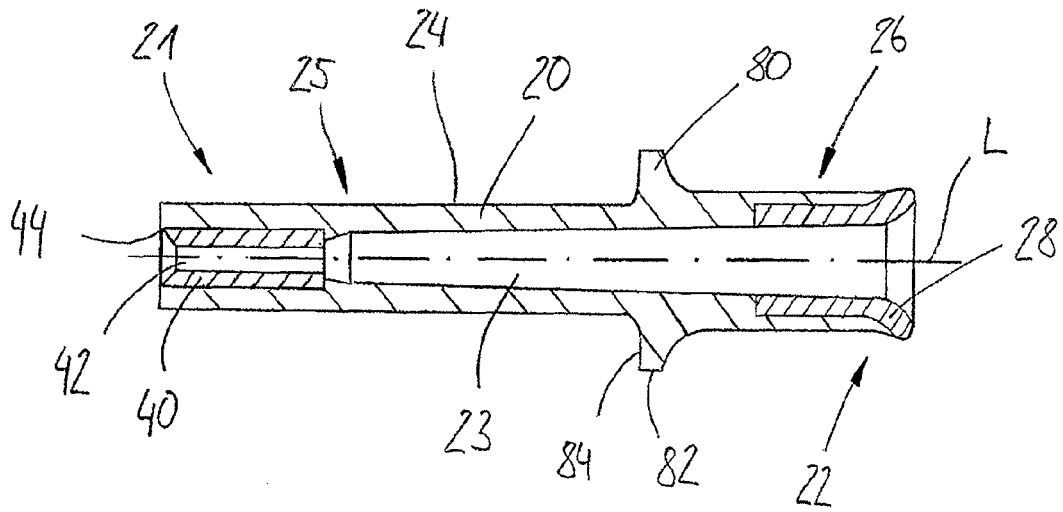
Figure 4:
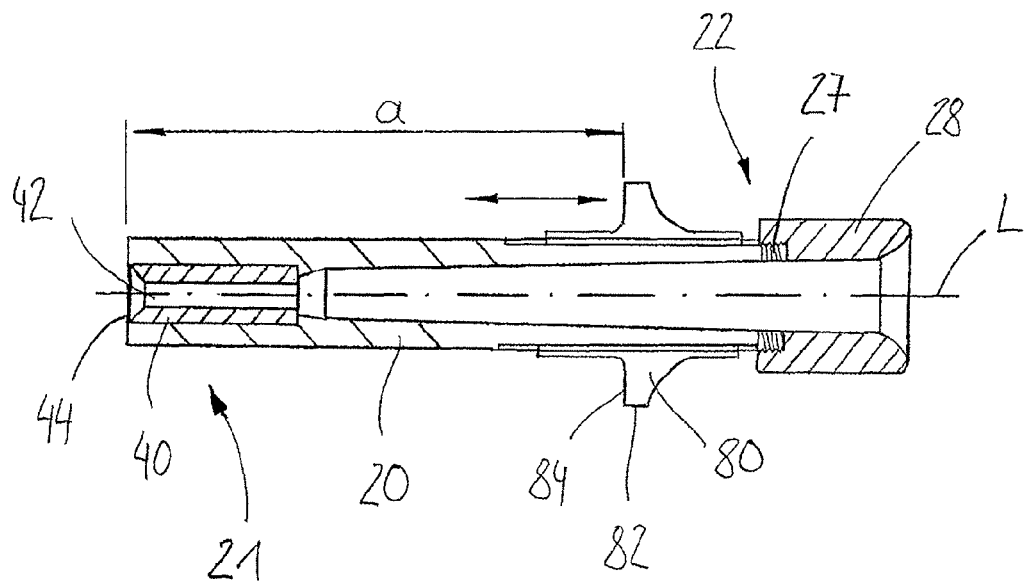
Figure 5:
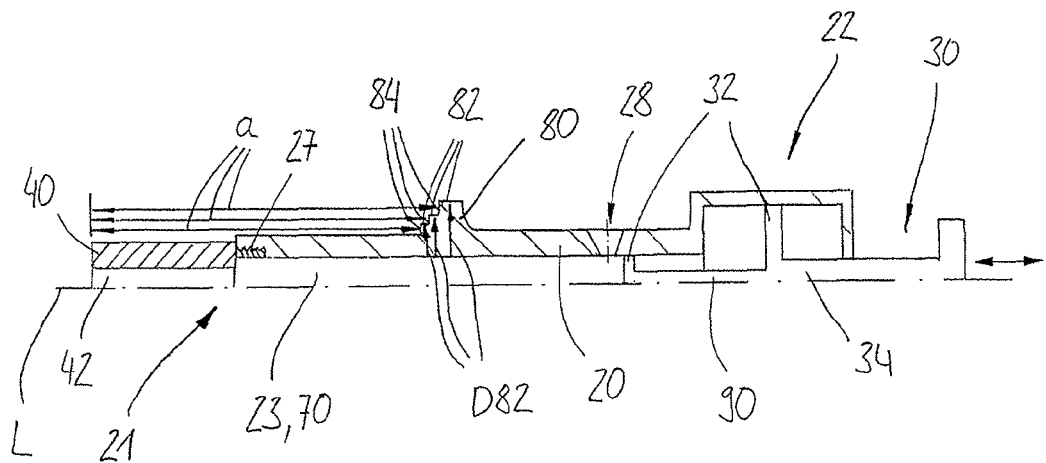
Figure 6:
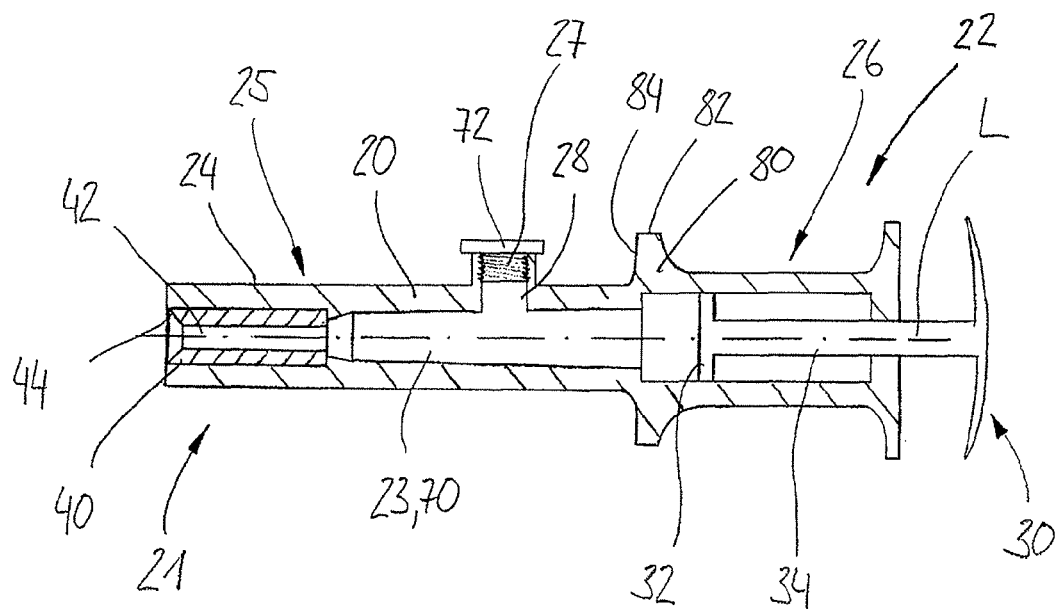
Figure 7A:
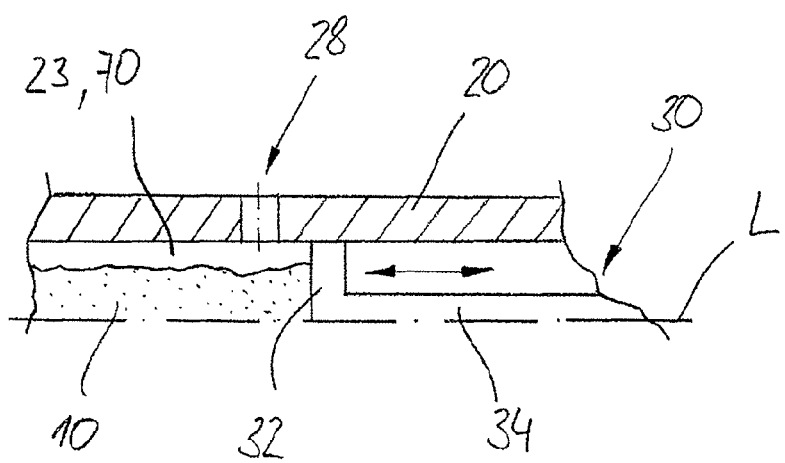
Figure 7B:
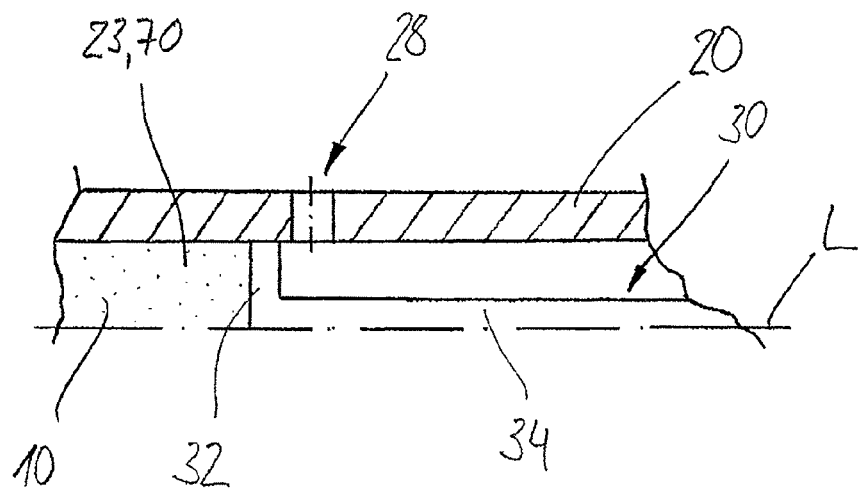

Further advantages and characteristics of the invention will become apparent from the following description of preferred embodiments of the cleaning device according to the invention, the medical device according to the invention as well as the use according to the invention, wherein reference is made to the figures, wherein individual characteristics of the individual embodiments may be combined within the scope if the invention, wherein in the figures:

FIG. 1: is a sectional view along a longitudinal axis showing a preferred embodiment of a cleaning device;

FIG. 2: is a preferred embodiment of a cleaning device, arranged in another element and connected to a pressure device;

FIG. 3: is a sectional view along a longitudinal direction showing a further preferred embodiment of a cleaning device;

FIG. 4: is a sectional view along a longitudinal axis showing a further preferred embodiment of a cleaning device having a centering unit, which may be displaced along the longitudinal axis;

FIG. 5: is a sectional view along a longitudinal axis showing a preferred embodiment of a cleaning device having an actuation device;

FIG. 6: is a sectional view along a longitudinal axis showing a further preferred embodiment of a cleaning device having an actuation device;

FIG. 7a: is a sectional view showing a further preferred embodiment of a cleaning device having an actuation device;

FIG. 7b: is a further view of the preferred embodiment of the cleaning device of FIG. 7a.

FIG. 1 shows a sectional view along a longitudinal axis L of a preferred embodiment of a cleaning device, representing a base body 20, which extends essentially along the longitudinal axis L. At a first end 21, the base body 20 has a receiving zone 40, which comprises a receiving channel 41 and is formed as a separate component. The receiving channel 41, which on one end faces a nozzle to be cleaned (not shown herein), is provided with a bevel 44. The receiving channel 42, which has a diameter D42, is connected to a main channel 23, which extends along the longitudinal direction L within the base body 20. The main channel 23 has a diameter D23, which throughout is greater than the diameter D42 of the receiving channel 42. At a second end 22, the main channel 23 terminates into an access zone 28. At an outer periphery 24, the base body 20 has a first arrangement zone 25 and a second arrangement zone 26. Between the first arrangement zone 25 and the second arrangement zone 26 the base body 20 essentially has a centering unit 80, which is provided with a radial stopper surface 82 and an axial stopper surface 84.

FIG. 2 shows a preferred embodiment of a cleaning device, arranged in another element 50 and connected to a pressure device 60. The other element 50 is a hand piece of a powder jet device, which is schematically represented. The hand piece has a nozzle tube 52 to be cleaned, which is arranged within a receiving channel 42 of a receiving section 40. The receiving zone 40 is located at a first end 21 of a base body 20. An access zone 28, in which or at which, respectively, a pressure device 60 is arranged, is located at a second end 22 of the base body 20.

FIG. 3 shows a sectional view along a longitudinal direction of a cleaning device of a further preferred embodiment. It essentially is the embodiment shown in FIG. 1, but herein an access zone 28 is formed as a separate component, which is form-fittingly and/or force-fittingly arranged in a base body 20.

FIG. 4 shows a further sectional view along a longitudinal axis L of a preferred embodiment of a cleaning device, and having a centering unit 82, which may be displaced along the longitudinal axis L. The centering unit 82 has a radial stopper surface 82 and an axial stopper surface 84. Between the radial stopper surface 82 and a beginning of a receiving channel 42 of a receiving section 42 there is a distance a, which may be displaced by way of displacing the centering unit 80 along the longitudinal axis L. The receiving zone 40 is formed as a separate component, which, within the base body 20, is arranged at a first end 21. To facilitate arrangement of another member, for example a nozzle tube (not shown herein), the receiving channel 42 has a bevel 44. At a second end 22, the base body 20 is connected to an access zone 28 by a thread 27.

FIG. 5 shows a sectional view along a longitudinal axis L of a preferred embodiment of a cleaning device having an actuation device 30. At a first end 21 of a base body 20, the cleaning device has a receiving zone 40, which is connected to the base body 2 by a thread 27. A receiving channel 42 is connected to a main channel 23. The main channel 23 also functions as a tank 70, which may be filled with a medium 10, for example a fluid, via an access zone 28. Transport of the medium 10 as well as a pressure built-up is done via the actuation device 30 or movement of a piston rod 34, respectively, to the left (cf. double arrow in FIG. 5). In the embodiment shown in FIG. 5 the piston rod 34 is attached to two pistons 32, which, in combination, form a pressure converter 90. The base body 20 has a centering unit 80, which is circumferentially located and has three radial stopper surfaces 84 and three axial stopper surfaces 82. Three centering diameters D82 and three distances a are formed therewith.

FIG. 6 shows a sectional view along of a longitudinal axis L of a further preferred embodiment of a cleaning device having an actuation device 30. At a first end 21 of the cleaning device, a receiving zone 40 is located, comprising a receiving channel 42 having a bevel 44. The receiving channel 42 extends in a main channel 23, which simultaneously is a tank 70 and which has an access zone 28, through which the main channel 23 or the tank 70, respectively, may be filled. The access zone 28 may be pressure- and liquid-tightly closed by a lid 27. Between a first arrangement zone 25 and a second arrangement zone 26, which represent different sections of an outer periphery 24, a centering unit 80 is located, which has a radial stopper surface 82 and an axial stopper surface 84. The actuation device 30, which comprises a piston rod 34 and a piston 32, and through which the pressure in the main channel 23 may be built up, is located adjacent to a second end 22 of the cleaning device. To facilitate operation, the actuation device 30 and the second receiving zone 26 suitably are ergonomically formed. It may easily be conceived that, alternatively, the piston rod 34 is not required to be guided out of the base body 20. Thus, it alternatively is provided, that the embodiment shown in FIG. 6, at the second end 22, is provided with a pressure connection (not shown), by means of which the actuation device 30 may be operated. An atmospheric pressure or a liquid pressure, which causes displacement of the piston rod 34, may be incorporated through the pressure connection.

FIG. 7a shows a sectional view of a further preferred embodiment of a cleaning device having an actuation device 30. Herein, emphasis is made on the position of the access sections 28 in relation to the piston 32 of the actuation device 30. By displacing a piston rod 34 to the left a medium 10, which is in a main channel 23 or in a tank 70, respectively, is also be displaced to the left. Initially no pressure built-up occurs since the main channel 23 or the tank 70, respectively, are not completely filled with the medium 10. The cleaning device is designed such that the actual pressure built-up of the medium 10 starts after the piston 32 has passed through the access zone 28, cf. FIG. 7b. Thus, a lid may be omitted, since the main channel 23 or the tank 70, respectively, will automatically be closed.

LIST OF REFERENCE NUMBERS

10 Medium, fluid
20 Base body
21 first end
22 Second end
23 Main channel
24 Outer periphery
25 First arrangement zone
26 Second arrangement zone
27 Thread
28 Access zone
30 Actuation device
32 Piston
34 Piston rod
40 Receiving zone
42 Receiving channel
44 Bevell
50 Further element, hand piece
52 Nozzle tube
60 Pressure device
70 Tank
72 Lid
80 Centering unit
82 Radial stopper surface
84 Axial stopper surface
90 Pressure converter
D23 Diameter of main channel
D42 Diameter of receiving channel
L Longitudinal axis
a Distance
D82 Centering diameter

The invention claimed is:

1. A cleaning device, especially for cleaning clogged nozzles of dental devices, having a base body, which comprises a main channel, wherein the main channel is configured for the transport of a medium, especially a fluid, characterized in that, the base body, at a first end, has a receiving zone, wherein the receiving zone is designed for the arrangement of another member, especially a clogged dental device, and
in that the main channel has an access zone, through which the medium may be fed into the main channel and/or the pressure thereof may be raised;
wherein the receiving zone is formed of a material which is softer than a material of the base body, and
wherein the material of the receiving zone has a hardness lower than 75 Shore.

2. The cleaning device according to claim 1, characterized in that, the receiving zone has a receiving channel, and in that a diameter of the main channel is greater than a diameter of the receiving channel.

3. The cleaning device according to claim 1, characterized in that, in and/or at the access zone a pressure device may be pressure-tightly arranged, by means of which the medium may be passed into the main channel and/or the pressure of the medium may be raised.

4. The cleaning device according to claim 1, characterized in that, the base body has an actuation device, through which the medium may be passed and/or the pressure of the medium may be raised.

5. The cleaning device according to claim 1, characterized in that, the base body, at an outer periphery, has a first and a second arrangement zone, wherein at least one cross section of the first arrangement zone is essentially round.

6. The cleaning device according to claim 1, characterized in that, the base body comprises at least one centering unit, which, at least in certain areas, extends essentially radial and/or parallel to a longitudinal direction of the base body, and which is designed for the orientation and/or centering of the base body relative to the other element, especially a hand piece of a dental device.

7. The cleaning device according to claim 6, characterized in that, the centering unit comprises at least one radial stopper surface and/or at least one axial stopper surface.

8. The cleaning device according to claim 6, characterized in that, the centering unit may be positioned and set on the base body along the longitudinal direction.

9. The cleaning device according to claim 1, characterized in that, the access zone is formed of a material, which is softer than a material of the base body.

10. The cleaning device according to claim 1, characterized in that, the receiving zone and/or the access zone is form-fittingly and/or force-fittingly connected to the base body.

11. The cleaning device according to claim 1, characterized in that, the base body comprises a pressure converter.

12. A medical apparatus having a cleaning device according claim 1.

13. The use of a cleaning device according to claim 1 in a medical apparatus.

* * * * *